(12) United States Patent
Lynn et al.

(10) Patent No.: US 11,890,090 B1
(45) Date of Patent: *Feb. 6, 2024

(54) ROTARY VALVE ASSEMBLIES AND METHODS OF USE FOR BREATH SAMPLE CARTRIDGE SYSTEMS

(71) Applicant: Hound Labs, Inc., Oakland, CA (US)

(72) Inventors: Michael Scott Lynn, Piedmont, CA (US); Joseph A. Heanue, Oakland, CA (US); Kevin M. Limtao, Temple City, CA (US); Jeffrey A. Schuster, Alameda, CA (US); Peter A. Holst, Los Altos, CA (US)

(73) Assignee: Hound Labs, Inc., Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/895,409

(22) Filed: Aug. 25, 2022

Related U.S. Application Data

(63) Continuation of application No. 16/655,182, filed on Oct. 16, 2019, now Pat. No. 11,426,097.

(60) Provisional application No. 62/821,900, filed on Mar. 21, 2019, provisional application No. 62/746,858, filed on Oct. 17, 2018.

(51) Int. Cl.
| | |
|---|---|
| *A61B 5/097* | (2006.01) |
| *F16K 1/36* | (2006.01) |
| *A61B 10/00* | (2006.01) |
| *F16K 1/42* | (2006.01) |
| *F16K 1/46* | (2006.01) |
| *F16K 31/524* | (2006.01) |

(52) U.S. Cl.
CPC ............... *A61B 5/097* (2013.01); *F16K 1/36* (2013.01); *F16K 1/42* (2013.01); *F16K 1/46* (2013.01); *F16K 31/52408* (2013.01); *A61B 2010/0087* (2013.01)

(58) Field of Classification Search
CPC . A61B 5/097; A61B 2010/0087; A61B 5/082; F16K 1/44; F16K 1/36; F16K 1/46; F16K 1/42; F16K 1/34; F16K 31/52408
See application file for complete search history.

(56) References Cited

U.S. PATENT DOCUMENTS

| | | | | |
|---|---|---|---|---|
| 3,086,833 A | * | 4/1963 | Clemens | C09B 67/0065 252/384 |
| 3,393,108 A | * | 7/1968 | Jones | A61B 5/097 222/1 |
| 3,676,072 A | * | 7/1972 | Krivis | G01N 31/22 436/93 |
| 4,133,202 A | * | 1/1979 | Marple | G01N 15/0255 96/417 |

(Continued)

*Primary Examiner* — David Colon-Morales
(74) *Attorney, Agent, or Firm* — Mahamedi IP Law LLP

(57) ABSTRACT

An example breath collection and sampling device disclosed herein comprises a cartridge housing having a breath capture module, and a rotary valve operatively coupling a mouthpiece with the breath capture module. The rotary valve can have an open position where breath of a user can pass through the rotary valve, across capture sites of the breath capture module, and into a vacuum port, and a closed position for sealing the breath capture module from fluid passing through the rotary valve, while allowing the breath capture module to be exposed to a reagent for subsequent analysis of contents within the captured breath.

13 Claims, 11 Drawing Sheets

(56) References Cited

U.S. PATENT DOCUMENTS

| | | | | |
|---|---|---|---|---|
| 4,232,667 A * | 11/1980 | Chalon | A61M 16/22 | 128/911 |
| 4,288,344 A * | 9/1981 | Reiss | G01N 31/22 | 534/565 |
| 4,292,978 A | 10/1981 | Guth | | |
| 4,771,005 A * | 9/1988 | Spiro | G01N 33/948 | 436/131 |
| 5,026,027 A * | 6/1991 | Hamilton | A61B 5/097 | 251/303 |
| 5,103,857 A * | 4/1992 | Kuhn | F16K 21/04 | 251/255 |
| 5,140,993 A * | 8/1992 | Opekun, Jr. | G01N 33/497 | 422/84 |
| 5,361,771 A * | 11/1994 | Craine | A61B 5/0813 | 73/23.3 |
| 5,589,346 A * | 12/1996 | Kanan | G01N 33/6887 | 436/174 |
| 5,922,610 A * | 7/1999 | Alving | G01N 33/0026 | 436/116 |
| 6,067,983 A * | 5/2000 | Stenzler | A61M 16/0493 | 128/204.23 |
| 6,326,159 B1 * | 12/2001 | Ullman | C07K 16/42 | 436/805 |
| 6,460,539 B1 * | 10/2002 | Japuntich | A62B 18/10 | 128/205.12 |
| 6,537,823 B1 * | 3/2003 | Smith | G01N 33/52 | 436/63 |
| 6,582,376 B2 * | 6/2003 | Baghdassarian | A61B 5/097 | 73/23.3 |
| 6,605,444 B1 * | 8/2003 | Klein | G01N 33/54386 | 435/287.7 |
| 7,059,349 B2 * | 6/2006 | Breda | F16K 11/0856 | 137/625.11 |
| 7,364,553 B2 * | 4/2008 | Paz | A61B 5/0878 | 600/529 |
| 7,547,285 B2 * | 6/2009 | Kline | A61B 10/0045 | 600/529 |
| 8,237,118 B2 * | 8/2012 | Prox | G01N 27/624 | 250/396 R |
| 8,586,932 B2 * | 11/2013 | Rousso | A61B 5/417 | 250/361 R |
| 8,705,029 B2 * | 4/2014 | Palmskog | F01D 5/048 | 356/301 |
| 8,707,758 B2 * | 4/2014 | Keays | G08B 5/22 | 73/23.3 |
| 8,955,366 B2 * | 2/2015 | Abraham-Fuchs | G01N 33/497 | 73/23.3 |
| 9,429,564 B2 * | 8/2016 | Beck | G01N 33/497 | |
| 9,617,582 B2 * | 4/2017 | Milton | C12Q 1/6804 | |
| 9,709,582 B1 * | 7/2017 | Gordon | G01N 33/582 | |
| 9,921,234 B1 * | 3/2018 | Lynn | G01N 33/948 | |
| 9,933,445 B1 * | 4/2018 | Lynn | G01N 33/948 | |
| 9,970,950 B1 * | 5/2018 | Lynn | G01N 33/557 | |
| 9,976,944 B2 * | 5/2018 | Olin | G01N 15/0255 | |
| 10,226,201 B2 * | 3/2019 | Ahmad | A61B 10/00 | |
| 10,557,563 B2 * | 2/2020 | Thurau | F16K 31/5286 | |
| 11,026,596 B1 * | 6/2021 | Lynn | A61B 5/087 | |
| 11,187,711 B1 * | 11/2021 | Lynn | B01L 7/52 | |
| 11,426,097 B1 * | 8/2022 | Lynn | F16K 1/36 | |
| 2002/0177232 A1 * | 11/2002 | Melker | G01N 33/497 | 436/151 |
| 2003/0153844 A1 * | 8/2003 | Smith | G01N 33/54373 | 600/573 |
| 2004/0043479 A1 * | 3/2004 | Briscoe | G01N 30/6095 | 435/288.5 |
| 2005/0105077 A1 * | 5/2005 | Padmanabhan | G01N 33/5094 | 356/39 |
| 2006/0094123 A1 * | 5/2006 | Day | G01N 33/948 | 436/93 |
| 2006/0257941 A1 * | 11/2006 | McDevitt | G01N 33/5302 | 435/7.2 |
| 2007/0031283 A1 * | 2/2007 | Davis | A61B 5/15087 | 422/400 |
| 2007/0077660 A1 * | 4/2007 | Glas | G01N 30/90 | 436/93 |
| 2008/0004542 A1 * | 1/2008 | Allen | C12P 7/28 | 600/532 |
| 2008/0045825 A1 * | 2/2008 | Melker | A61B 5/083 | 600/529 |
| 2009/0017555 A1 * | 1/2009 | Jehanli | G01N 33/526 | 436/501 |
| 2011/0086364 A1 * | 4/2011 | Takkinen | G01N 33/948 | 435/7.1 |
| 2013/0006068 A1 * | 1/2013 | Gemer | A61B 10/0051 | 600/314 |
| 2013/0102018 A1 * | 4/2013 | Schentag | G01N 21/05 | 435/25 |
| 2013/0165806 A1 * | 6/2013 | Wondka | A61B 5/0836 | 600/532 |
| 2014/0094391 A1 * | 4/2014 | McDevitt | A61B 10/0051 | 600/572 |
| 2014/0276100 A1 * | 9/2014 | Satterfield | A61B 5/7271 | 600/476 |
| 2014/0288454 A1 * | 9/2014 | Paz | A61B 5/4845 | 600/532 |
| 2014/0366609 A1 * | 12/2014 | Beck | G01N 33/497 | 73/23.3 |
| 2015/0025407 A1 * | 1/2015 | Eichler | G01N 33/0037 | 128/204.23 |
| 2015/0033824 A1 * | 2/2015 | Hammarlund | A61B 5/082 | 73/23.3 |
| 2015/0065901 A1 * | 3/2015 | Bhatnagar | A61B 5/097 | 600/543 |
| 2015/0265184 A1 * | 9/2015 | Wondka | A61B 5/082 | 600/532 |
| 2015/0305651 A1 * | 10/2015 | Attariwala | A61B 5/4845 | 600/532 |
| 2015/0369830 A1 * | 12/2015 | Crichlow | G01N 33/948 | 436/501 |
| 2016/0000358 A1 * | 1/2016 | Lundin | A61M 16/105 | 128/204.23 |
| 2016/0299125 A1 * | 10/2016 | Cristoni | G01N 30/7233 | |
| 2017/0128692 A1 * | 5/2017 | Christopher | A61B 5/097 | |
| 2017/0197213 A1 * | 7/2017 | Nielsen | B01L 3/527 | |
| 2017/0303822 A1 * | 10/2017 | Allsworth | A61B 5/097 | |
| 2017/0303823 A1 * | 10/2017 | Allsworth | A61B 10/00 | |
| 2018/0120278 A1 * | 5/2018 | Hoorfar | G01N 33/0031 | |
| 2018/0243523 A1 * | 8/2018 | Nason | A61B 5/0803 | |
| 2020/0147333 A1 * | 5/2020 | Stoll | A61M 16/0858 | |
| 2020/0245899 A1 * | 8/2020 | Heanue | A61B 5/082 | |
| 2020/0278275 A1 * | 9/2020 | Turgul | G01N 33/497 | |
| 2020/0300876 A1 * | 9/2020 | Lynn | G01N 33/497 | |
| 2021/0330516 A1 * | 10/2021 | Letourneau | A61B 5/6826 | |

* cited by examiner

US 11,890,090 B1

ROTARY VALVE ASSEMBLIES AND METHODS OF USE FOR BREATH SAMPLE CARTRIDGE SYSTEMS

CROSS REFERENCE TO RELATED APPLICATIONS

This application is a Continuation of U.S. patent application Ser. No. 16/655,182, filed on Oct. 16, 2019, which claims the benefit of priority to each of (i) U.S. Provisional Patent Application No. 62/746,858, filed on Oct. 17, 2018, and (ii) U.S. Provisional Patent Application No. 62/821,900, filed on Mar. 21, 2019; the aforementioned priority applications being hereby incorporated by reference in their respective entirety.

FIELD OF THE INVENTION

The present disclosure is directed generally to rotary valve assemblies that are configured for use in breath same cartridge systems. The rotary valve assemblies are adapted to translate from an open configuration to a closed configuration as desired.

SUMMARY

Some embodiments of the present disclosure can be directed to a device for breath capture and analysis. The device can comprise a cartridge housing comprising a breath capture module, and a rotary valve operatively coupling a mouthpiece with the breath capture module, the rotary valve having an open position where breath of a user can pass through the rotary valve, across capture sites of the breath capture module, and into a vacuum port, and a closed position for sealing the breath capture module from fluid passing through the rotary valve, while allowing the breath capture module to be exposed to a reagent for further analysis of one or more target chemicals that may be present in the breath. As used herein, the term fluid refers to the liquid phase or the gas phase.

Some embodiments of the present disclosure can be directed to a rotary valve that comprises a valve body operatively coupling a mouthpiece with a breath capture module, the valve body having a central aperture providing a path for the communication of breath across the breath capture module, and a sealing member is capable of sealing the breath capture module to prevent the breath from contacting the breath capture module. The valve body is configured to translate between an open position where the breath of a user passes through the central aperture of the valve body, across capture sites of the breath capture module, and into a vacuum port, and a closed position where the sealing member is sealing the breath capture module from fluid passing through the rotary valve, while allowing the breath capture module to be exposed to a reagent from a port associated with the breath capture module.

Some embodiments of the present disclosure can be directed to a rotary valve that comprises a valve body comprising a central aperture providing a path for the communication of breath across the breath capture module when the rotary valve is in an open position, and a sealing surface that is capable of created a seal against at least a portion of an upper surface of the breath capture module to prevent the breath from contacting the breath capture module when the rotary valve is in a closed position.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Generally speaking, the present disclosure is directed to rotary valves that are configured for use in breath sample cartridge systems. A rotary valve of the present disclosure can operatively couple a mouthpiece of a breath sample collection system to a breath capture module of the breath sample collection system. The rotary valve can translate between an open position and a closed position. When the rotary valve is in the open position the exhaled breath of a user can pass from the mouthpiece, through the rotary valve, and across the breath capture module. When the rotary valve is in the closed position, one or more sealing surfaces of the rotary valve abut inputs or outputs of the breath capture module, effectively preventing the breath of the user from passing over the breath capture module (or any other fluid such as ambient air). Further, when the rotary valve is in the closed position, the breath capture module can be exposed to a reagent for extraction and subsequent analyses of components within the collection breath. While the term "rotary valve" is used herein to describe exemplary embodiments, it will be understood by persons of ordinary skill in the art that other mechanisms that provide similar functionality may alternatively be utilized.

Figure 1:
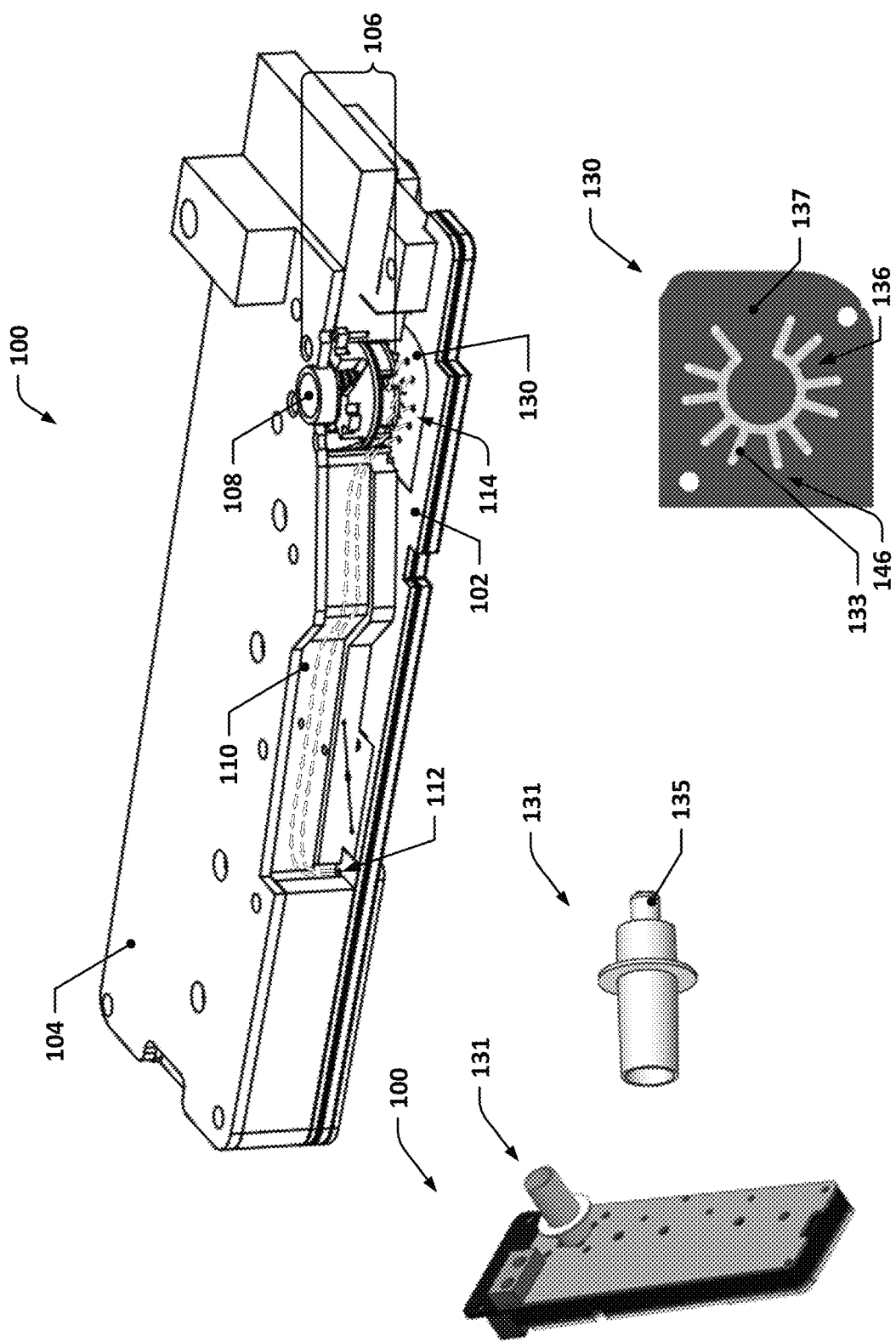
FIG. 1 illustrates an example breath sample cartridge system constructed in accordance with the present disclosure, specifically illustrating a breath capture module and rotary valve.

FIG. 1 depicts an example breath sample cartridge system 100 having a substrate 102 attached to a larger cartridge housing 104 that includes a rotary valve 106 having a breath sample receiving port 108, also referred to as a central aperture, which may, as discussed herein, be interfaced with a saliva trap and/or mouthpiece 131. The cartridge housing 104 may, as shown, have a vacuum passage 110 that is fluidically positioned between the exhaust passages 112 and a vacuum port 114 during breath sample collection.

The vacuum port 114 may, in turn, be fluidically coupled with a vacuum pump or pumps, e.g., within a handheld unit that may be connected with a cartridge during sample collection.

Figure 2:
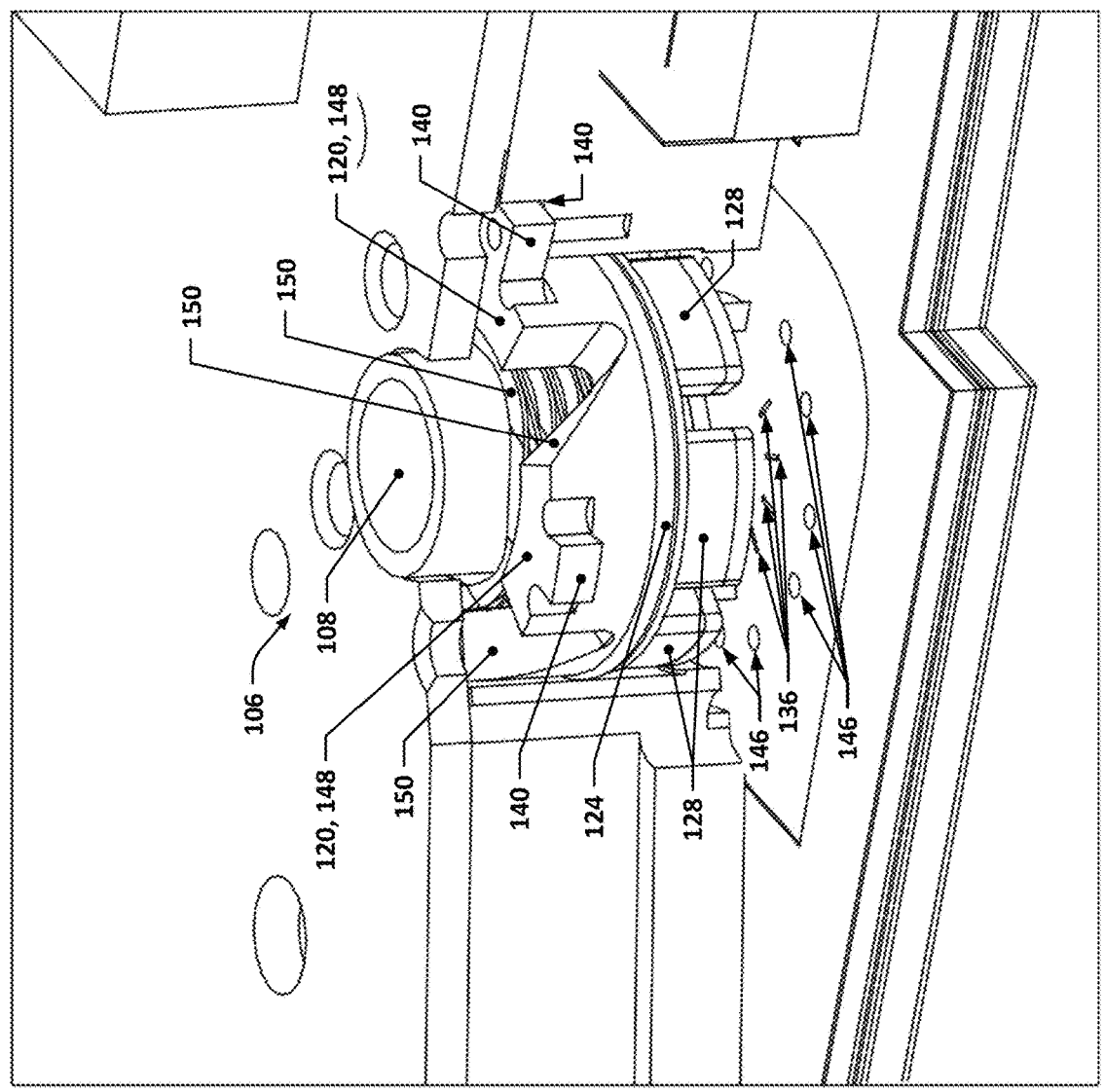
FIG. 2 is a perspective view of an example rotary valve of the present disclosure installed in an example breath sample cartridge system.
Figure 3:
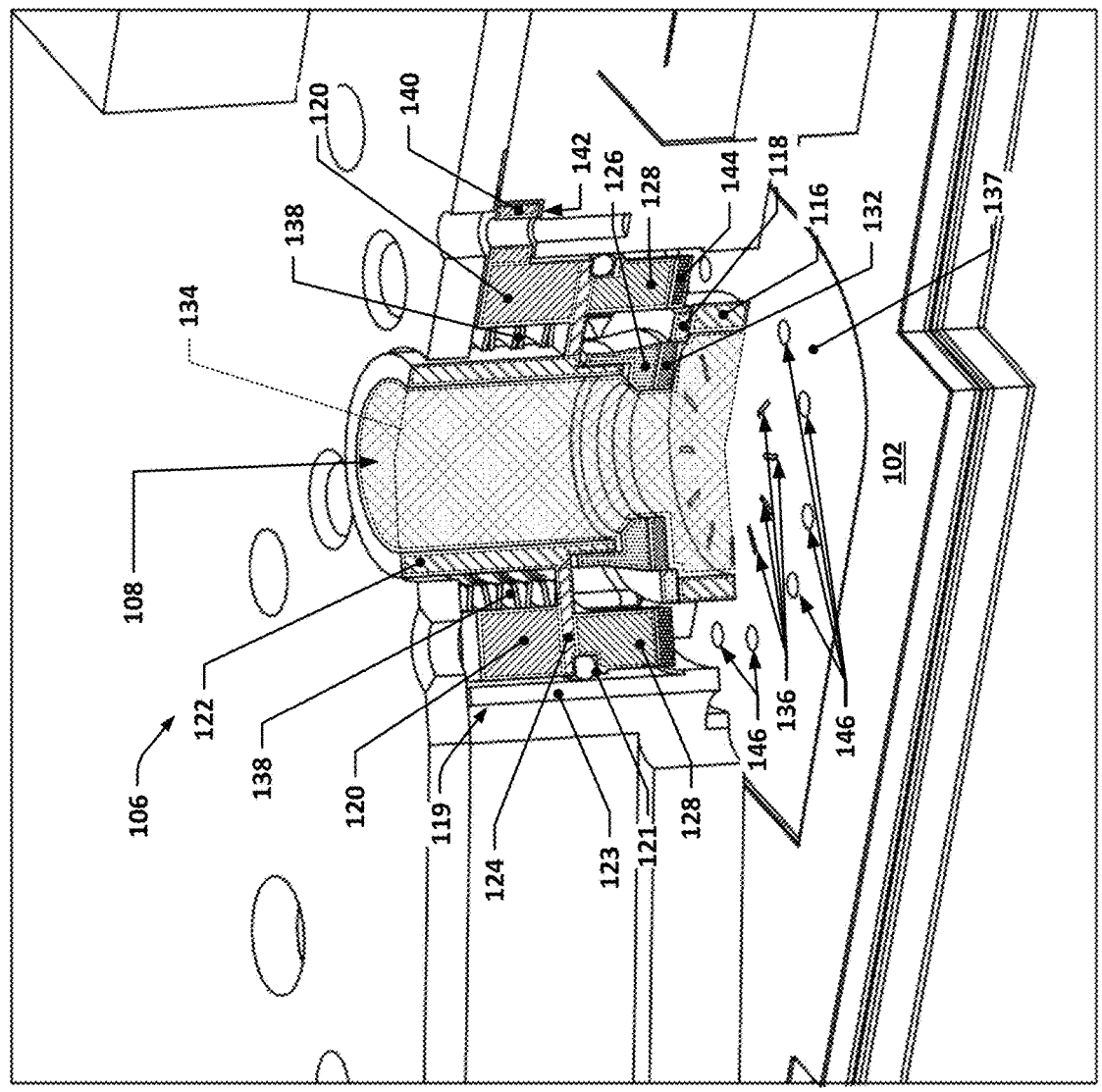
FIG. 3 is a perspective, cross-section view of the example rotary valve in an open configuration/position.
Figure 4:
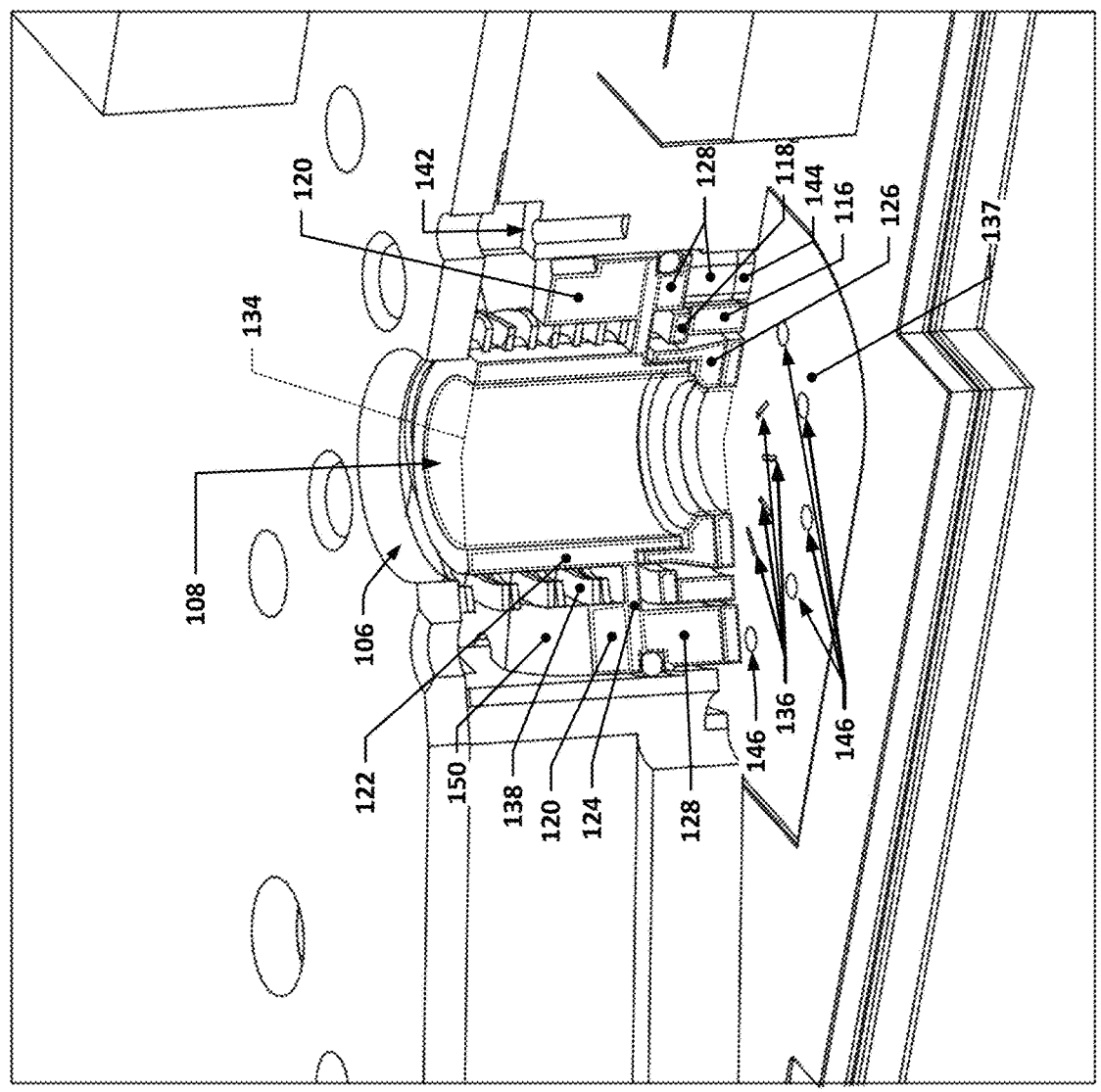
FIG. 4 is a perspective, cross-section view of the example rotary valve in a closed configuration/position.

FIG. 2 depicts a close-up of the rotary valve 106 of FIG. 1; FIGS. 3 and 4 show additional cutaway views of the rotary valve 106 in both an "open" configuration (FIG. 3) and a "closed" configuration (FIG. 4). The depicted valve structure is only one example of a valve structure that may be used with the droplet traps discussed herein; other valve structures may be used to provide similar functionality. In some implementations, no valve structure may be used at all, and the functionality provided by the valve structure may be provided by other means.

The following description will reference FIGS. 2-4 collectively. In the depicted rotary valve 106, the rotary valve 106 has a first portion that is fixed relative to the substrate 102. The first portion, in this example, includes the annular lower wall 116 and the annular lower wall seal 118. In general, the rotary valve 106 operatively couples a mouthpiece 131 with the breath capture module 130. In general, the first and second portions of the rotary valve are referred to as the valve body 119.

In some embodiments, a gasket, such as an o-ring 121 is disposed between the valve body 119 and a rotary valve receiver 123 of the cartridge housing 100. The o-ring 121 provides a seal between the valve body of the rotary valve and the rotary valve receiver in the cartridge housing.

The depicted rotary valve 106 may also include a second portion that is movable relative to the first portion and the substrate 102. The second portion, in this example, includes various features (shown in cross-section in FIGS. 3 and 4), such as, for example, an annular outer wall 120, a tubular inner structure 122, a circular base 124, a collar 126, and lower risers 128.

The tubular inner structure 122 defines a passageway into which a saliva trap, mouthpiece (see example mouthpiece 131), or other adapter may be inserted in order to allow a breath sample to be blown into a breath capture module 130. In general, the rotary valve 106 operatively couples a mouthpiece 131 with the breath capture module 130. That is, the rotary valve 106 provides a pathway for communication of the breath of a user to, and through, the breath capture module 130. In some embodiments, the mouthpiece 131 comprises a stem 135 that is configured to fit into the central aperture/breath sample receiving port 108 of the rotary valve 106.

In the open configuration/position, the breath of a user can pass through the rotary valve 106, across capture sites 133 of the breath capture module 130, and into a vacuum port 114 as a remainder of the breath (that portion which is not captured in the breath capture module 130) exits the breath capture module 130 from the exhaust ports 146.

The inner surfaces of the tubular inner structure 122, collar 126, and annular upper valve seal 132 of the second portion and the annular lower wall 116 and the annular lower wall seal 118 of the first portion may define a plenum volume 134 through which the breath sample may be flowed before flowing through the impaction ports 136 of the breath capture module 130. The plenum volume 134 may be generally sealed between the breath sample receiving port 108 and the impaction ports 136 when the valve structure is in the "open" configuration so as to allow a positive pressure to be developed within the plenum volume 134 during breath sampling.

In the depicted rotary valve 106, the second portion is able to translate along the center axis of the rotary valve 106, e.g., along a direction perpendicular to the substrate 102. A compression spring 138 may apply force to the second portion, e.g., by being compressed between the housing of the cartridge and the second portion, that urges the second portion towards the substrate 102 and into the "closed" configuration. In some embodiments, the compression spring 138 includes a plurality of stacked wave springs. In the closed configuration/position, the rotary valve seals the breath capture module 130 from fluid, such as breath, passing through the rotary valve 106, while allowing the breath capture module 130 to be exposed to a reagent. The exposure of the breath capture module 130 to reagents is beyond the scope of this disclosure.

The second portion may have a plurality of radial tabs 140 (also referred to as protrusions) that extend outwards from the annular outer wall 120 and that may rest on ledges 142 in the housing of the cartridge when the rotary valve 106 is in the "open" configuration. If the second portion is rotated about the center axis of the plenum 134 by a sufficient amount, e.g., 20°, this may cause the radial tabs 140 to no longer rest on the ledges 142, freeing the second portion to translate along that center axis towards the substrate 102 due to the force exerted by the compression spring 138. The lower risers 128 may be equipped with exhaust port seals 144, which may be made of a compliant material, as may be the case with the annular upper valve seal 132, in order to seal against the substrate 102 when in the closed configuration. In some embodiments, the exhaust port seals 144 seal the plurality of exhaust ports 146 of the breath capture module 130. The annular upper valve seal 132 seals against the impaction ports 136 of the breath capture module 130. To be sure, the exhaust port seals 144 and the annular upper valve seal press against elements of an upper surface 137 of the breath capture module 130. In various embodiments, the terminal ends of the exhaust port seals 144 comprise a closed-cell foam. The terminal end of the annular upper valve seal 132 can also comprise closed-cell foam. While closed-cell foam has been disclosed, other similar materials can likewise be utilized in accordance with the present disclosure. To be sure, other materials such as polymers, elastomers, hybrid materials (including foams and blends), as well as any other similar natural or composite materials ranging from flexible or rigid can also be used. To be sure, any material that would be known to one of ordinary skill in the art with the present disclosure before them can be selected that is capable of being used to create a seal against the exhaust ports 146 and the impaction ports 136.

Collectively, the exhaust port seals 144 and the annular upper valve seal 132 may be referred to generally in some embodiments as a sealing surface or member. In general, the sealing surface or member is capable of creating a seal against at least a portion of the upper surface 137 of the breath capture module 130.

In the depicted examples, the annular lower wall seal 118 is also made of a compliant material to allow the annular lower wall seal 118 and the annular upper valve seal 132 to seal against each other radially when in the closed configuration. In other configurations, the annular lower seal may simply seal radially against the rigid plastic of the annular lower wall 116. In yet other configurations, the annular upper valve seal 132 and the annular lower wall seal 118 may be provided by a single piece of material, which may be partially die cut such that the portion that corresponds with the annular upper valve seal 132 may tear free of the portion that corresponds with the annular lower wall seal 118 when the rotary valve 106 is transitioned to the closed configuration.

Figure 5:
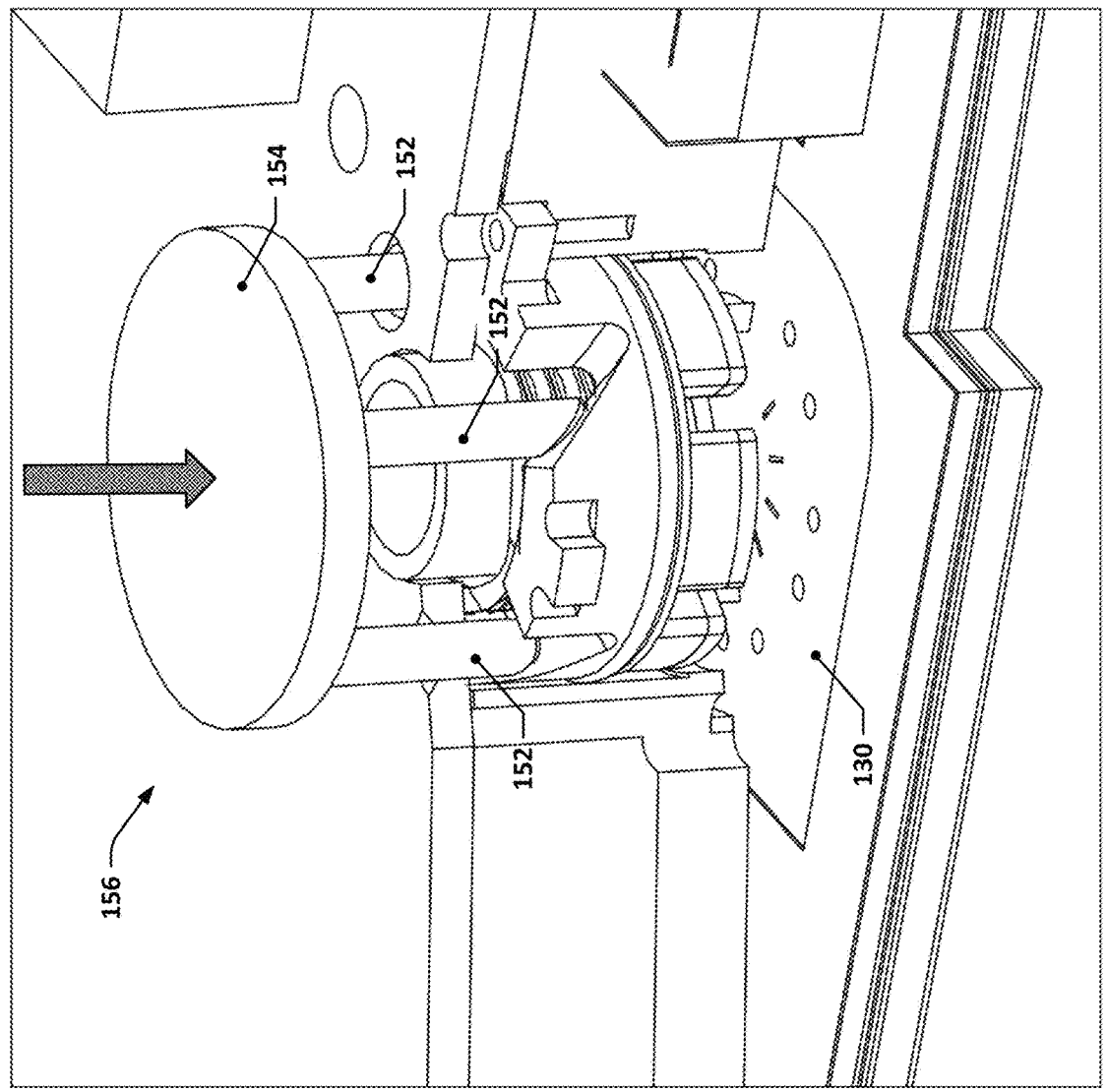
FIGS. 5 and 6 collectively illustrate the use of a tool to close the rotary valve.
Figure 6:
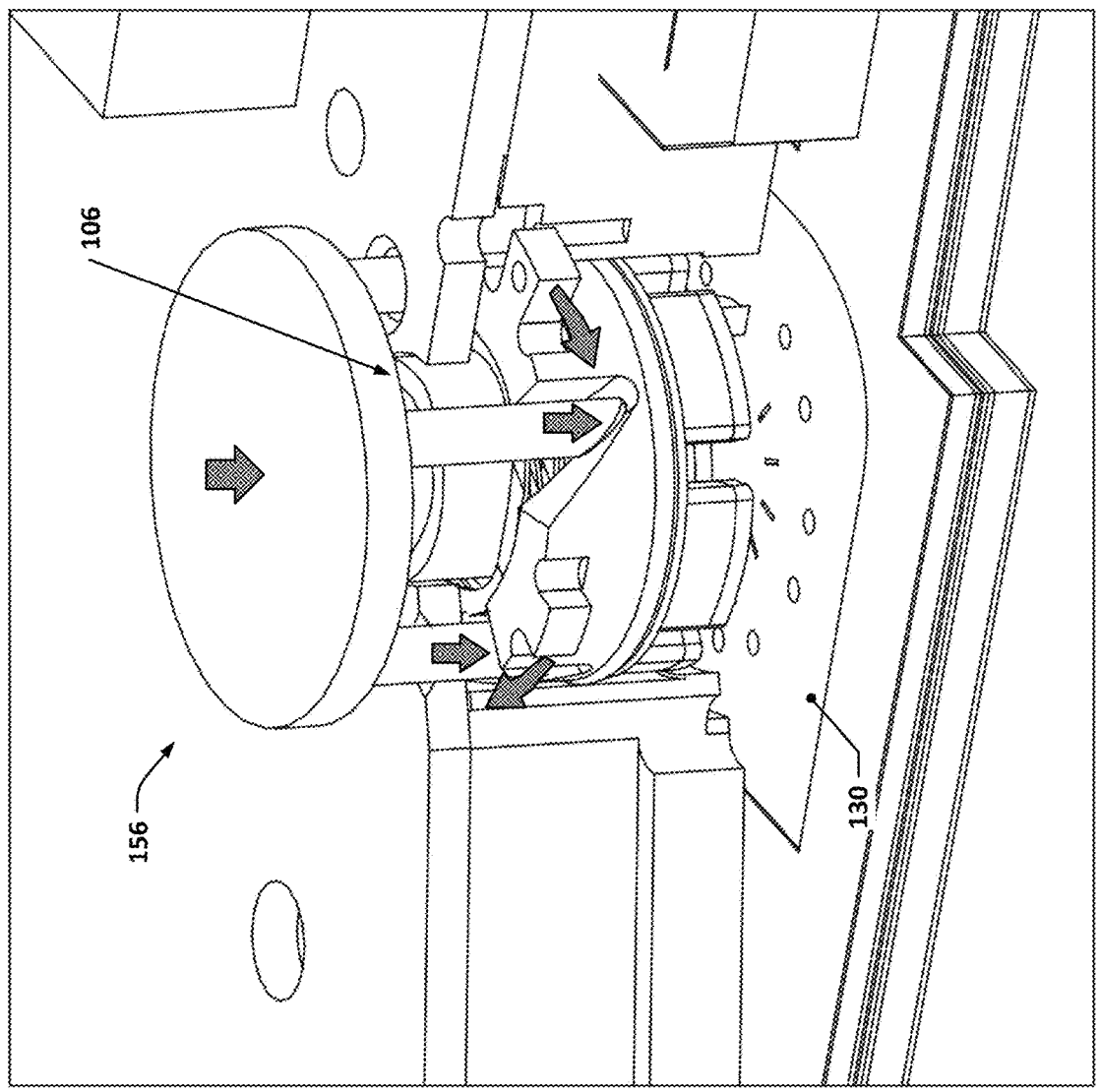
Figure 7:
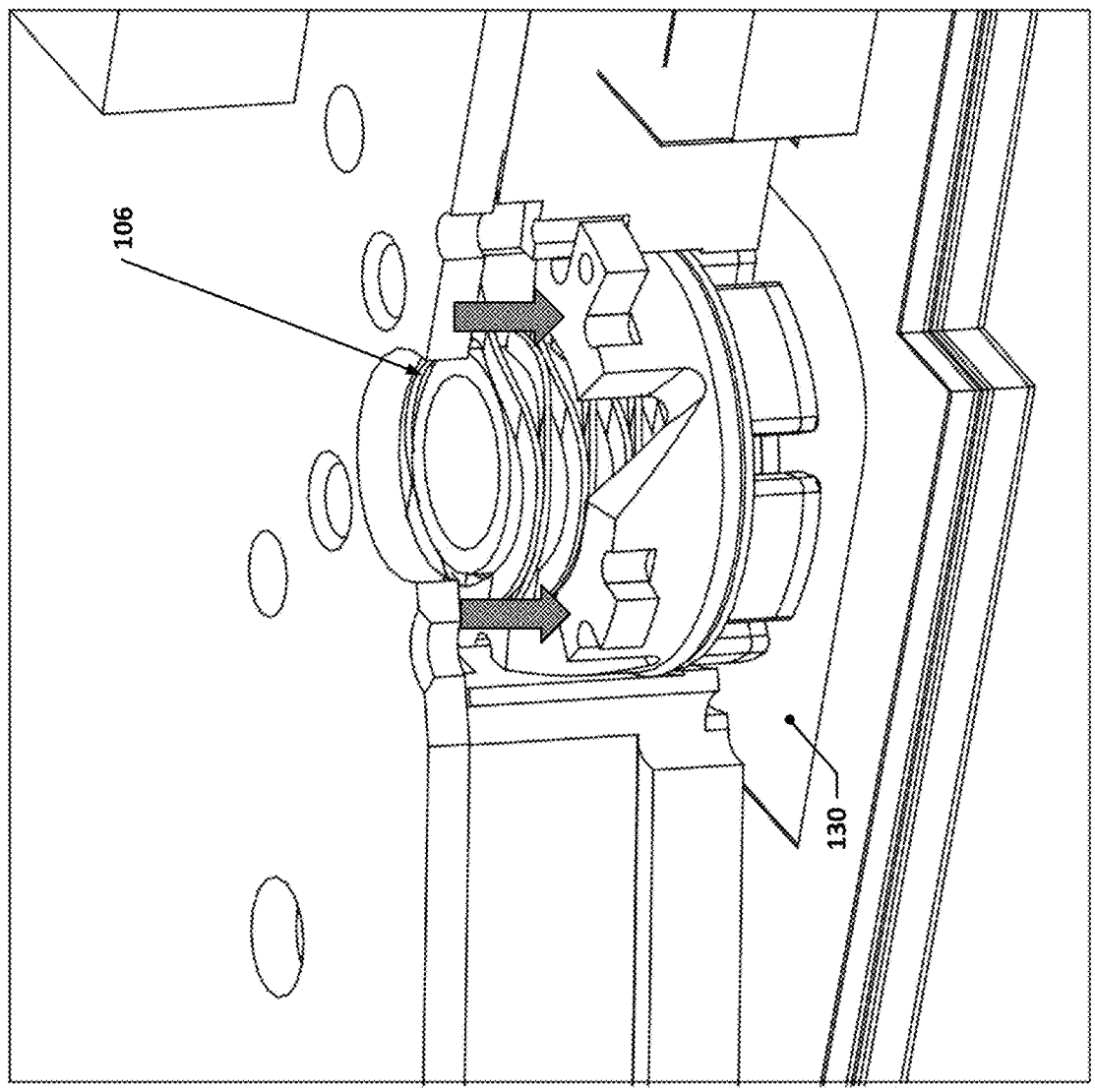
FIG. 7 illustrates the example rotary valve in a closed configuration/position after use of the tool.

The depicted rotary valve 106 thus simultaneously seals the impaction ports 136 and the exhaust ports 146 of the exhaust passages (the second ends) when transitioned to the closed configuration; this seals the captured droplets (from the breath sample) inside of the breath capture module 130, allowing for the collected sample in the captured droplets to be eluted or otherwise fluidically manipulated without leaking back out of the impaction ports 136 or through the exhaust passages 112. FIGS. 5 through 7 collectively depict the closure of the valve structure in the depicted examples.

Referring back to FIG. 2, it will be noted that the annular outer wall 120 includes a series of crenellations 148 that each have a sloped side 150. Additionally, the housing may have a hole located above each such sloped surface, allowing posts 152 (referring back to FIG. 5) attached to a load distributor 154 of actuator key 156 to be inserted therethrough and engage with the sloped sides 150. When compressive force is applied to the load distributor 154, the posts 152 are urged downward onto the sloped sides 150, causing the second portion to rotate so that the posts "slide" down the sloped sides 150—in this example, such rotation is clockwise (when looking along the compression direction) and causes the radial tabs 140 to rotate clear of the ledges 142 so that the latching mechanism provided by the radial tabs and ledges releases and allows the second portion to move relative to the first portion and enter the "closed" configuration, as shown in FIGS. 6 and 7.

The rotary valve and breath capture components discussed herein can be utilized in a breath sample capture and analysis system. In exemplary embodiments, when the rotary valve is in the closed position, the captured breath sample in the breath collection module can be subject to additional analysis on a cartridge. Elution or other means for capturing target components in the collected breath can be utilized for collecting a sample on a cartridge for further analysis. Additionally, means for concentrating a target component can also be utilized. In exemplary embodiments, the cartridge can be a single-use microfluidic cartridge.

Figure 8:
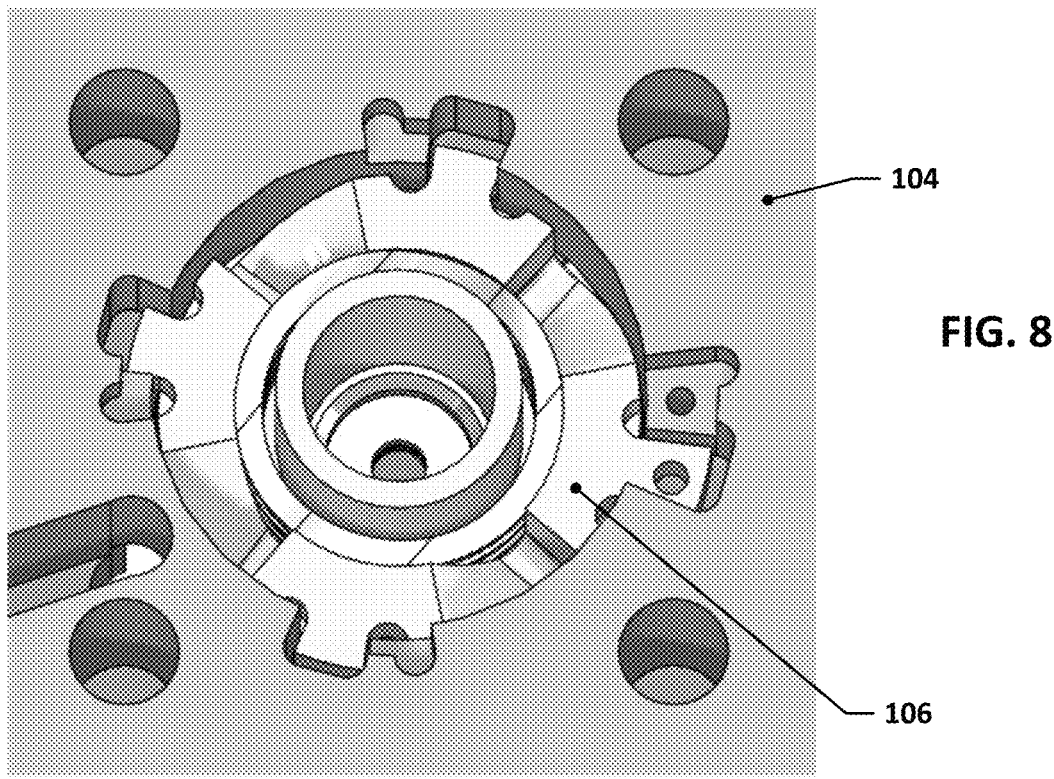
FIG. 8 depicts an exemplary view of an actuated rotary valve in a cartridge housing.
Figure 9:
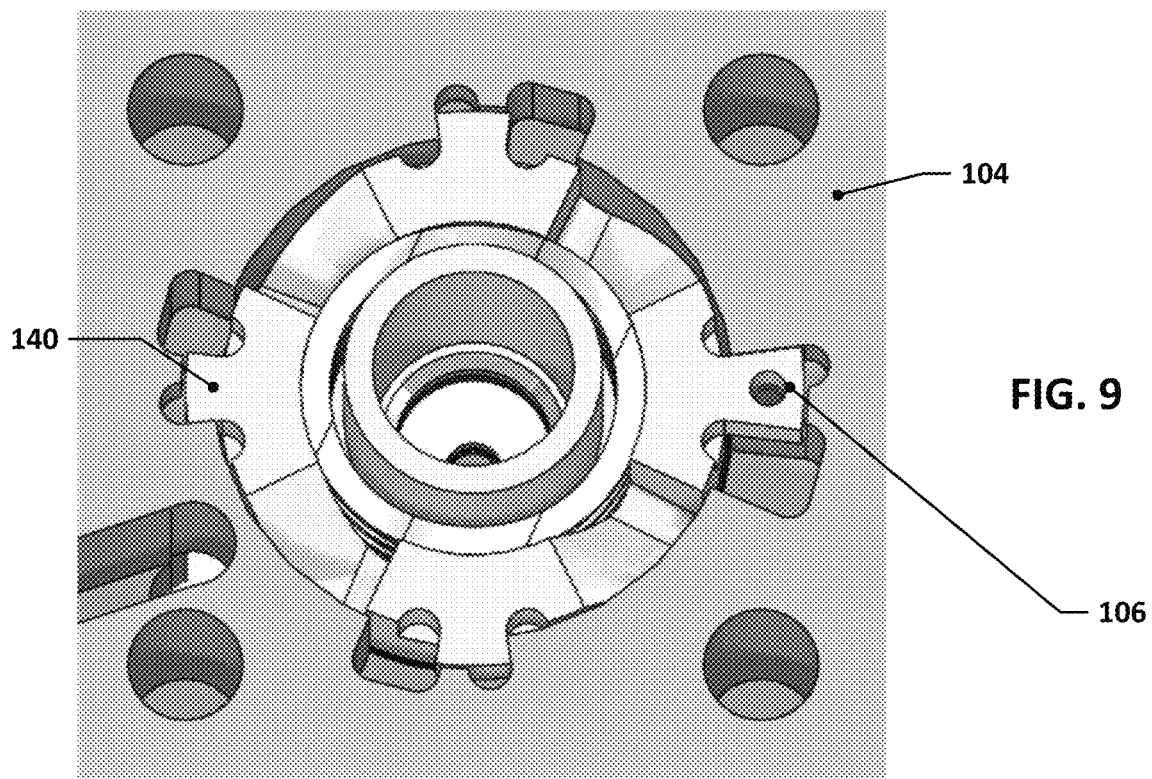
FIG. 9 depicts an exemplary view of a non-actuated rotary valve in a cartridge housing.

FIG. 8 depicts an exemplary view of an actuated rotary valve 106 in a cartridge housing 104. FIG. 9 depicts an exemplary view a non-actuated rotary valve 106 in a cartridge housing 104. As shown in the two figures, the radial tabs 140 of rotary valve 140 translate when moving from a non-actuated (open) position to an actuated (closed) position.

Figure 10:
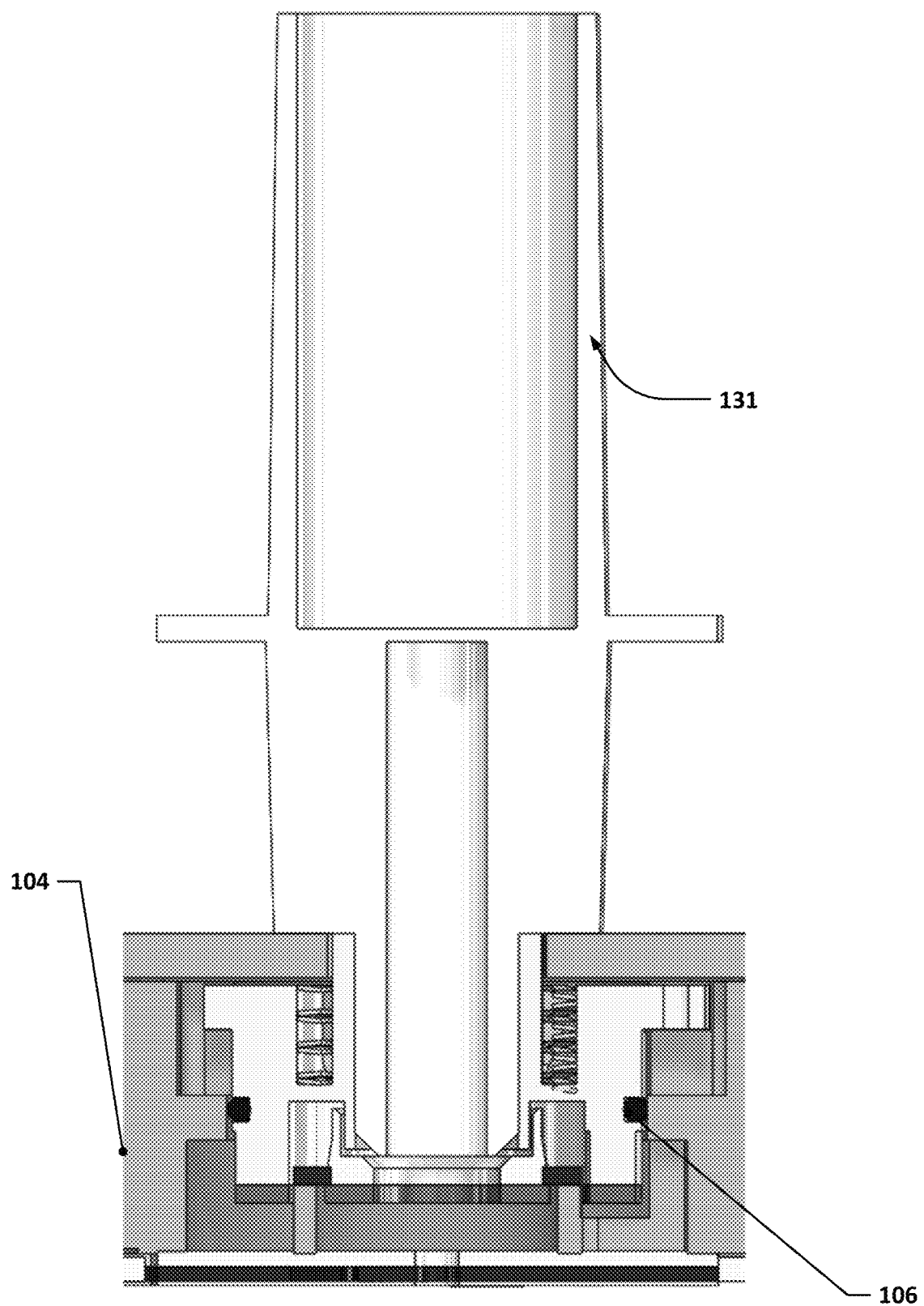
FIG. 10 depicts an exemplary cross-sectional side view of a rotary valve with a mouthpiece attached.

FIG. 10 depicts an exemplary cross-sectional side view of a rotary valve 106 in a cartridge housing 104, with attached mouthpiece 131. As discussed herein, a user blows into mouthpiece 131 until a target amount of breath is captured by the device. Then the rotary valve 106 is engaged to seal off mouthpiece 131 such that no further air can enter through it into the breath capture module and components of the cartridge. It will be understood by persons of ordinary skill in the art that the components in the exemplary figure are not necessary depicted according to scale. That is, the size of the components can be altered with respect to one another and still be within the scope of this disclosure.

Figure 11:
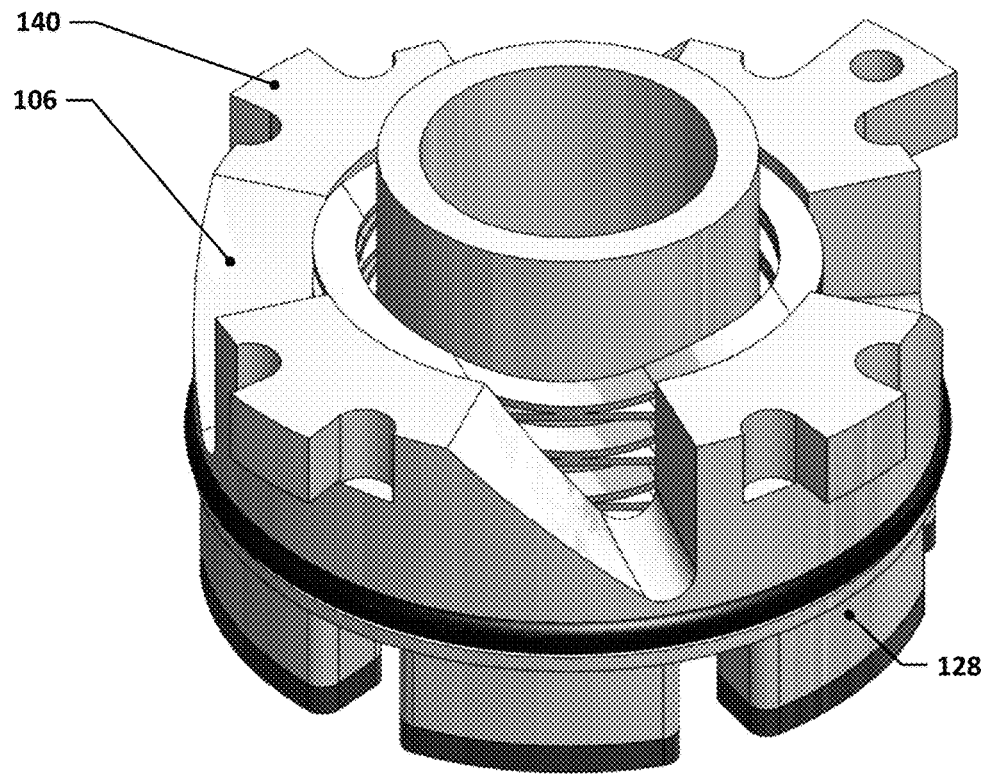
FIG. 11 depicts an exemplary isometric view of a rotary valve from the top and side.
Figure 12:
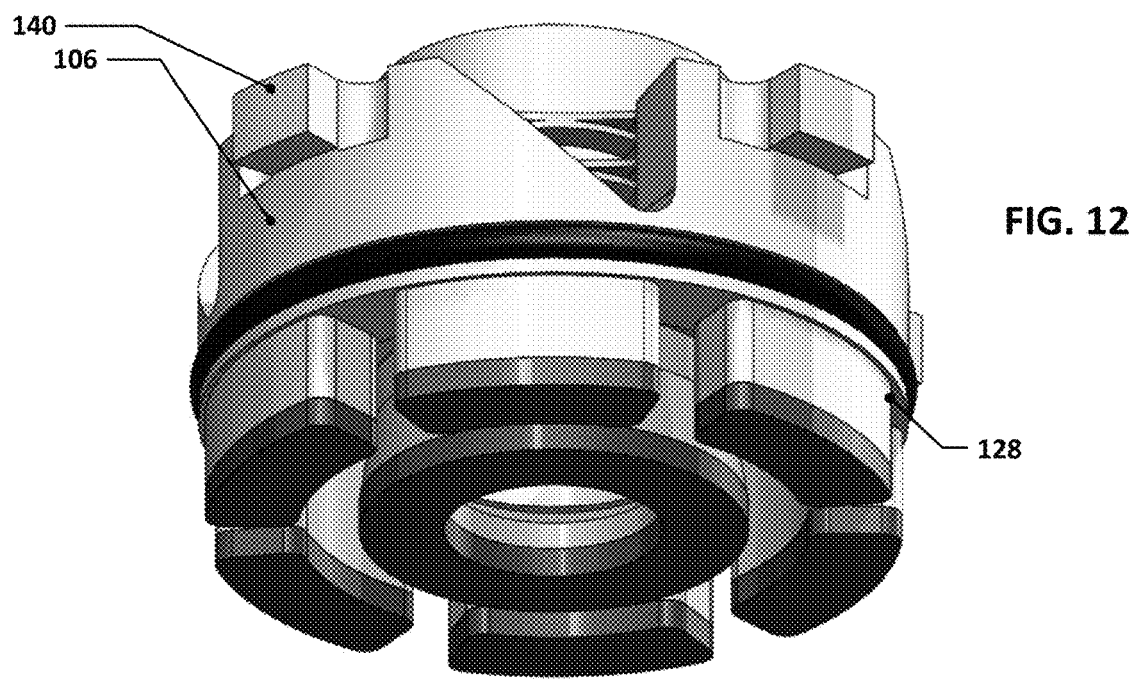
FIG. 12 depicts an exemplary isometric view of an underside of a rotary valve.

FIG. 11 depicts an exemplary isometric view of rotary valve 106. FIG. 12 depicts an exemplary isometric view of an underside of rotary valve 106. In each view, rotary valve 106 has at least lower risers 128 and radial tabs 140 extending outward from the annular outer wall of rotary valve 106.

Figure 13:
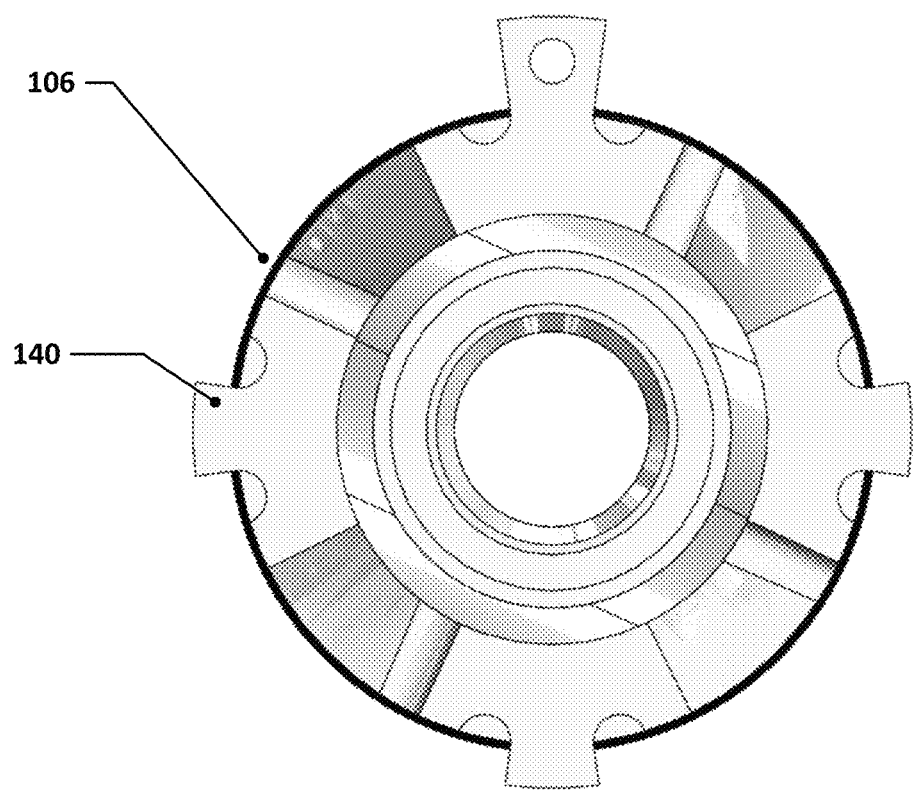
FIG. 13 depicts an exemplary top view of a rotary valve.
Figure 14:
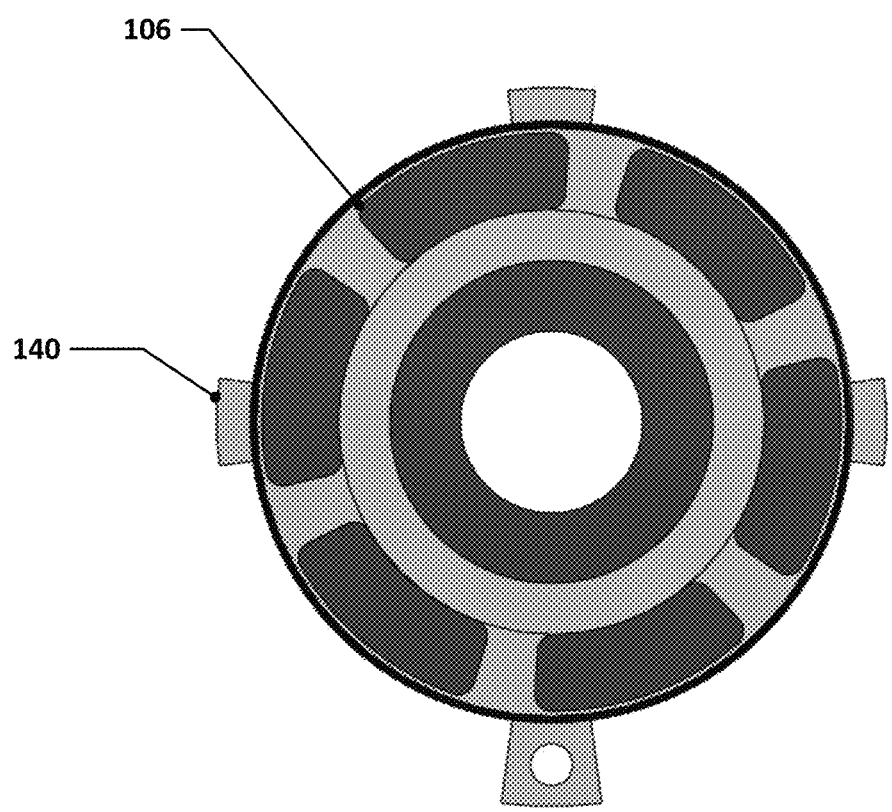
FIG. 14 depicts an exemplary underside view of a rotary valve.

FIG. 13 depicts an exemplary top view of rotary valve 106, and FIG. 14 depicts an exemplary underside view of rotary valve 106. The rotary valve 106 depicted in these exemplary views is the same as rotary valve 106 depicted in FIG. 11 and FIG. 12.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

In this description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form.

What is claimed is:

1. A device, comprising:
   a cartridge housing comprising a breath capture module; and
   a rotary valve operatively coupling a mouthpiece with the breath capture module, the rotary valve having a valve body with a central aperture, the valve body coupled to the cartridge housing via a spring, the rotary valve having:
      an open position where breath of a user can pass through the rotary valve, across capture sites of the breath capture module, and into a vacuum port; and
      a closed position for sealing the breath capture module from fluid passing through the rotary valve, while allowing the breath capture module to be exposed to a reagent.

2. The device according to claim 1, wherein the central aperture of the rotary valve is configured to receive a stem of the mouthpiece.

3. The device according to claim 1, wherein rotation of the rotary valve from the open position to the closed position causes protrusions of the valve body to rotate, allowing exhaust port seals and an annular upper valve seal to move downwardly to cover inputs and outputs of the breath capture module.

4. The device according to claim 3, wherein the protrusions are configured to rest on ledges of the cartridge housing when the rotary valve is in the open position.

5. The device according to claim 4, wherein the protrusions do not rest on the ledges when the rotary valve is in the closed position.

6. The device according to claim 5, wherein the exhaust port seals and the annular upper valve seal comprise gaskets that seal the inputs and outputs of the breath capture module.

7. The device according to claim 1, further comprising a gasket that provides a seal between the valve body of the rotary valve and a rotary valve receiver in the cartridge housing.

8. A rotary valve, comprising:
   a valve body comprising:
      a central aperture providing a path for the communication of breath into a breath capture module when the rotary valve is in an open position; and
      a sealing surface that is configured to create a seal against at least a portion of an upper surface of the breath capture module to prevent the breath from flowing into the breath capture module when the rotary valve is in a closed position; and a spring coupling the valve body to a cartridge housing, the valve body being configured to translate along an axis about which the valve body is configured to rotate within the cartridge housing.

9. The rotary valve according to claim 8, wherein when the rotary valve is in the open position the breath of a user passes across capture sites of the breath capture module, and into a vacuum port.

10. The rotary valve according to claim 8, wherein a reagent is flowable through the breath capture module without the reagent exiting the breath capture module via the inputs or outputs of the breath capture module when the rotary valve is in the closed position.

11. The rotary valve according to claim 8, wherein the sealing surface comprises exhaust port seals and an annular upper valve seal comprising a closed-cell foam that engages with inputs or outputs of the breath capture module.

12. The rotary valve according to claim 8, wherein the sealing surface prevents the breath from moving across capture sites of the breath capture module.

13. The rotary valve according to claim 8, wherein the central aperture of the valve body is configured to receive a stem of a mouthpiece.

\* \* \* \* \*